(12) United States Patent
Jones et al.

(10) Patent No.: US 7,676,070 B2
(45) Date of Patent: Mar. 9, 2010

(54) DEVICE FOR ON-LINE DATA ACQUISITION IN THREE-DIMENSIONAL POSITRON EMISSION TOMOGRAPHY

(75) Inventors: William F. Jones, Knoxville, TN (US); Johnny Reed, Clinton, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1301 days.

(21) Appl. No.: 11/130,631

(22) Filed: May 16, 2005

(65) Prior Publication Data

US 2005/0253074 A1 Nov. 17, 2005

Related U.S. Application Data

(60) Provisional application No. 60/571,399, filed on May 14, 2004.

(51) Int. Cl.
*G06K 9/00* (2006.01)
(52) U.S. Cl. .................. 382/128; 382/131; 382/132
(58) Field of Classification Search ............. 382/128, 382/131
See application file for complete search history.

(56) References Cited

U.S. PATENT DOCUMENTS 6,442,670 B2 * 8/2002 Acton et al. ................. 712/28
6,754,763 B2 * 6/2004 Lin ........................... 710/317

OTHER PUBLICATIONS

Jones, et al., LSO PET/SPECT Spatial Resolution: Critical On Line DOI Rebinning Methods and Results, 2001 IEEE, 0-7803-6503-8/1, pp. 16-54-16-58.
Jones, et al., First Time Measurement of Transaxial Resolution for a New-Sensitivity PET Prototype Using 5 LSO Panel Detectors, 0-7803-7636-6/06, 2003 IEEE, all pages.
International Search Report including Notification of Transmittal of the International Search Report, International Search Report and Written Opinion of the International Searching Authority.
W. Jones et al., "Next Generation PET Data Acquisition Architectures," IEEE MIC Conf. Rec., Oct. 1996.

(Continued)

*Primary Examiner*—Tom Y Lu
(74) *Attorney, Agent, or Firm*—Peter L. Kendall (57) ABSTRACT

A device for improved on-line histogramming of data acquired in a Positron Emission Tomography (PET) scan. The device is a Smart DRAM (SD) PCI card, of which more than one can be used in combination within a PC-based architecture for on-line histogramming. The SD PCI card is applied as either of a Gating Buffer, a histogramming card, and a normalization buffer. The Gating Buffer card alternately stores an arriving PET data packet stream into two dedicated DRAM banks. The two DRAM banks store and retransmit the packet stream in the order of arrival for an entire physiological cycle. The histogramming SD RMW PCI cards provide a very high rate of histogramming. The extendible daisy-chain of SD RMW PCI cards supports large memory banks across potentially hundreds of SD RMW PCI cards. Under a single PC, a multiple PCI Expansion chassis is employed such that a large number of PCI cards are supported.

15 Claims, 5 Drawing Sheets

OTHER PUBLICATIONS

W. Jones, "PETLINK_guideline_G8.pdf," CPS Innovations, Oct. 14, 1999. See: http://www.cpspet.com/bjones.nsf.

M. Casey et al., "A Component Based Method for Normalization in Volume PET," 3D Conference Proceedings, Aixles-bains, 1995.

W. Jones, "Real-time Event Stream Correction for Patient Motion in Clinical 3-D PET," IEEE MIC Conf. Rec., Nov. 2001.

P. Bloomfield et al., "The Design and Implementation of a Motion Correction Scheme for Neurological PET," Phys. Med. Bio., 2003, pp. 959-978, v. 48.

R. Fulton et al., "Event-by-Event Motion Compensation in 3D PET," IEEE MIC Conf. Rec., Oct. 2003.

M. Conti et al., "Implementation of Time-Of-Flight on CPS HiRez PET Scanner," CPS Innovations.

* cited by examiner

DEVICE FOR ON-LINE DATA ACQUISITION IN THREE-DIMENSIONAL POSITRON EMISSION TOMOGRAPHY

CROSS-REFERENCE TO RELATED APPLICATIONS

This application claims the benefit of U.S. Provisional Application No. 60/571,275, filed May 14, 2004.

STATEMENT REGARDING FEDERALLY SPONSORED RESEARCH OR DEVELOPMENT

Not Applicable

BACKGROUND OF THE INVENTION

1. Field of Invention

The present invention pertains to the field of Positron Emission Tomography (PET). More particularly, this invention is directed to a dedicated memory device for extremely flexible and general purpose support of on-line event-by-event normalization, real-time physiological gating, unity (+/−) histogramming, and weighted histogramming.

2. Description of the Related Art

Various techniques are used for medical imaging. Positron emission tomography (PET) is one of several popular methods in radiology because of its ability to non-invasively study physiological processes and structures within the body. PET is a nuclear imaging technique used in the medical field to assist in the diagnosis of diseases. PET allows the physician to examine the whole patient at once by producing pictures of many functions of the human body unobtainable by other imaging techniques. In this regard, PET displays images of how the body works (physiology or function) instead of simply how it looks. PET is considered the most sensitive, and exhibits the greatest quantification accuracy, of any nuclear medicine imaging instrument available at the present time. Applications requiring this sensitivity and accuracy include those in the fields of oncology, cardiology, and neurology.

In PET, short-lived positron-emitting isotopes, referred to as radiopharmaceuticals, are injected into a patient. When these radioactive drugs are administered to a patient, they distribute within the body according to the physiologic pathways associated with their stable counterparts. As the radiopharmaceutical isotopes decay in the body, they discharge positively charged particles called positrons. Upon discharge, the positrons encounter electrons, and both are annihilated. As a result of each annihilation event, gamma rays are generated in the form of a pair of diametrically opposed photons approximately 180 degrees (angular) apart. After the PET scanner detects these annihilation "event pairs" over a period of time, the isotope distribution in a cross section of the body is reconstructed. These events are mapped within the patient's body, thus allowing for the quantitative measurement of metabolic, biochemical, and functional activity in living tissue. More specifically, PET images (often in conjunction with an assumed physiologic model) are used to evaluate a variety of physiologic parameters such as glucose metabolic rate, cerebral blood flow, tissue viability, oxygen metabolism, and in vivo brain neuron activity.

For the current state-of-the-art in PET, critical technical challenges to data acquisition are frequently encountered. Clinical PET places a demanding burden on the electronic data acquisition architecture, especially when using larger, higher sensitivity detector arrays coupled with demands for high patient throughput. Pure list-mode data acquisition, in which gamma-pair-coincidence event packets are simply stored to disk in the order detected, can have limited acceptance due to either too-slow event-packet collection speeds and/or too-slow post-acquisition processing. The typical resolution for this problem, which is well documented in the literature, has been to perform histogramming (+/− unity to memory) in an on-line manner. For example, projection space "sinograms" are generated during the acquisition while the patient is still in the tomograph. Still, this solution alone shows several limitations when upcoming requirements for modern large-array PET detectors are considered—i.e., requirements such as dynamic studies, continuous bed motion, physiological gating, time-of-flight, and correction for patient motion. In the clinical setting, demands for high-patient throughput combined with these more complex data acquisition modalities result in a critical need for very capable and flexible electronic architectures to support on-line processing of the PET data stream.

One example of a long-axis, high-count-rate PET is described by Wienhard, et al., "The ECAT HRRT: Performance and First Clinical Application of the New High Resolution Research Tomograph," *IEEE Trans. Nucl. Sci.*, vol. 49, pp. 104-110 (2002). Another example of long-axis, high-count-rate PET is described by Jones, et al., "First Time Measurement of Transaxial Resolution for a New High-Sensitivity PET Prototype Using 5 LSO Panel Detectors," *IEEE NSS/MIC Conf. Rec.*, 2002. For an example of work in support of list-mode continuous bed motion in PET, see Townsend, et al., "Continuous bed motion acquisition for an LSO PET/CT scanner" *IEEE NSS/MIC Poster*, 2004 Rome. As an example of recent work in support of time-of-flight, refer to the work by Conti, et al., "Implentation of Time-of-Flight on CPS HiRez PET Scanner," *IEEE NSS/MIC Oral Presentation*, 2004 Rome. For work in the field of list-mode correction of patient motion, see the article by Fulton, et al., "Event-by-event motion compensation in 3D PET", *IEEE MIC Conf Rec.*, October 2003.

So as broad progress in PET continues, important challenges must be met in digital electronic architectures to bring these multiple, complex data-acquisition modalities into the clinical world of high-patient throughput. As a basis for progress, note Section VIII from this 1996 article which proposes the use of quad-interleaved DRAM for fast on-line PET histogramming: Jones, et al., "Next generation PET data acquisition architectures," *IEEE MIC Conf Rec.*, (1996).

BRIEF SUMMARY OF THE INVENTION

The present invention is a device for improved on-line histogramming of data acquired in a Positron Emission Tomography (PET) scan. The device of the present invention permits very fast read-modify-write (RMW, +/− unity and weighted) histogramming memory cycles, and permits very large amounts of RMW memory to be effectively controlled from a single PC motherboard running a single operating system (OS). In support of this fast histogramming into very large memory banks, the present invention also is configurable for on-line buffering of the coincidence packet stream, i.e., "gating buffer" which allows "bad beat" rejection and real-time phase-driven segmentation as needed for physiological cycles such as cardiac and respiratory. In addition, the present invention also provides an effective on-line mechanism for incorporating individual normalization correction factors into each coincidence event packet.

The present invention is a Smart DRAM (SD) peripheral component interconnect (PCI) card, of which more than one can be used in combination within a PC-based architecture for on-line histogramming. The SD PCI card is applied in a plurality of ways. Specifically, the SD PCI card is used as either of a Gating Buffer, a histogramming card, or a look up table (LUT) for normalization correction factors.

The Correction Factor LUT SD PCI card (SD CF LUT) serves to insert a 16-bit correction factor into arriving packets prior to packet retransmittal. These correction factors are retrieved from local RAM as each coincidence event packet arrives, using the contents of the arriving packets to form an index (address) into the local RAM. These correction factors serve to correct for PET detector variability in gamma detection efficiency, i.e., "normalization." The retransmitted packets are expanded in size to provide room for the inserted correction factor.

The Gating Buffer card alternately stores an arriving PET data packet stream into two dedicated DRAM banks. The two DRAM banks store and retransmit the packet stream in the order of arrival for an entire physiological cycle. This buffering enables on-line rejection of "bad-beat" cycles and serves the more complex needs of real-time cardiac/respiratory gating.

The SD RMW PCI cards provide a very high rate of histogramming. The extendible daisy-chain of SD RMW PCI cards supports large memory banks across potentially hundreds of SD RMW PCI cards. Under control of a single PC, a PCI Expansion chassis is employed such that a large number of PCI cards are supported. This off-the-shelf PCI expansion chassis system (StarFabric) is itself extendible allowing hundreds of PCI slots to be accessed from a single PC.

The present invention is further applicable to rapid dynamic, dynamic-gated, continuous bed motion, time-of-flight (TOF), gated-TOF, and correction for patient motion, and all in an on-line manner while the patient remains in the tomograph. In addition to on-line capability, the present invention further supports both list-mode-only data acquisition as well as for rapid replay in post-acquisition histogramming of previously collected list-mode data.

For effective index/offset control into the potential Terabytes of DRAM space, frame-offset tag packets are used. As a means to direct which frame or phase-segment portion of the bin-space is accessed for RMW activity, these offset-control tag packets are input to the Gating Buffer card under control of application software. The offset packets are intermixed with bin-address event packets, all from the Gating Buffer FC output port for reception by the down-stream SD RMW PCI cards. The bin-offset values within these tag packets are received and used by each downstream SD-RMW-resident FPGA to instantly direct histogramming into the designated projection frame throughout the array of SD RMW PCI cards. The FPGA on each SD RMW PCI card in the chain is directed from the PC operating system via FPGA-resident PCI-loaded registers to respond to only a designated card-size portion of the available projection-data bin space. This bin space is spread across all the SD RMW PCI cards in the chain. Thus, the offset-control tag-packet mechanism is an effective means to instantly direct bin-address activity into any part of the RMW daisy chain via minimal PCI interaction.

The component architecture internal to each SD RMW PCI card includes a single field programmable gate array (FPGA) in communication with RAM and with the input/output (I/O) flow, including I/O via at least one Fibre Channel (FC) and a PCI interface. Each of a plurality of DRAM modules is independently in communication with the FPGA to permit independent and simultaneous direct memory access (DMA) to each bank, thus optimizing throughput. The FPGA is in communication with each local Fibre Channel port. Each port consists of a transceiver, typically fiber optic, and a serializer/deserializer (SERDES) chip. Also provided in communication with the FPGA is a first in, first out (FIFO) memory chip.

In the histogramming SD PCI card, i.e., SD RMW, the FPGA architecture includes independent DRAM Controllers for actively accessing dedicated DRAM modules for read-modify-write (RMW) transactions. These RMW transactions take two forms. For +/− unity RMW, the transactions involve adding unity to or subtracting unity from individual bins in the DRAM memory. These Unity RMW bins are 2's complement integer values stored as either 8-bit or 16-bit. For Weighted RMW, the transactions involve adding a correction factor to or subtracting a correction factor from individual bins in the DRAM memory. These Weighted RMW bins are 2's complement "block floating" values and are typically stored as 32-bit only.

Also for the SD RMW application, the DRAM bin-address space is quad-interleaved with the assistance of an FPGA-resident Interleave Router. This Router supports quad-interleaving by distributing, according to address-value content, bin-address data packets to each of the four FPGA-resident FIFO blocks and their associated DRAM modules. These FPGA-resident FIFO blocks are provided to greatly reduce the chance of packet pile-up and loss. FPGA-resident bin-address offset control is applied to assist in real-time control of multiple-frame dynamic or multiple-phase-segment gated studies. After histogramming is completed for a DRAM-resident projection space and as the projection-space data is read, the FPGA automatically reorders the internal quad-interleaved organization during DMA transfer out to PCI bus, eliminating the need for subsequent user re-assembly of the final projection data set.

In the Gating Buffer card, the FPGA and DIMMs are applied without interleaving or histogramming. The Gating SD PCI card is provided primarily to buffer packets in the order of arrival into one of two DRAM banks. While one bank is loading with data packets arriving in real time via FC input port, the other bank is unloading via FC output port. Data packet output is controlled by operating system-resident application code which drives autonomous FPGA-resident DMA controllers. The PET packet stream arriving at the Gating Buffer is interspersed with both LOR (event) packets and other non-event (tag) packets. Tag packet content includes elapsed milliseconds, cardiac R-wave, and respiratory phase data.

For the correction factor look-up function (i.e., SD CF LUT), the local DRAM is loaded prior to the start of the acquisition with a PET normalization correction matrix, which is an array of scalar values which reflect the reciprocal of the varied gamma detection efficiencies as pre-determined for each detector pair. As each detector-pair packet arrives via an FC port from the PET Gantry, each respective scalar correction value, in block-floating format, is extracted from the local DRAM content. The index into the local DRAM is formed by the FPGA from the detector-pair packet content, namely, the crystal-pair indexes. An extracted correction factor value is loaded, i.e., inserted, into a designated field within the detector-pair packet. This modified packet with correction value, which is potentially larger than its original size, is then transmitted for further processing via the out-going FC port.

For the weighted histogramming function, i.e., SD Weighted RMW, each DRAM-resident RMW bin is a 32-bit 2's complement block-floating value. The event packets input via the FC port are intermixed with conventional tag packets. These event (non-tag) packets are called weighted bin-address event packets. These weighted bin-address event packets contain not only the traditional Prompt/Delayed (P/D) bit but also a bin-address field and the correction-value field. A correction value is added/subtracted to/from the respective bin in DRAM memory, depending on the P/D bit. In this mode of operation with 32-bit bins, the bin-address value is applied as a quad-byte index into local DRAM. Because both the correction value and the bin content are treated as block floating, the FPGA performs only signed-integer arithmetic for the RMW memory cycles.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

A device for improved on-line histogramming of data acquired in a Positron Emission Tomography (PET) scan is disclosed. The device of the present invention permits very fast read-modify-write (RMW, +/− unity and weighted) histogramming memory cycles, and permits very large amounts of RMW memory to be effectively controlled from a single PC motherboard running a single operating system (OS).

Figure 1:
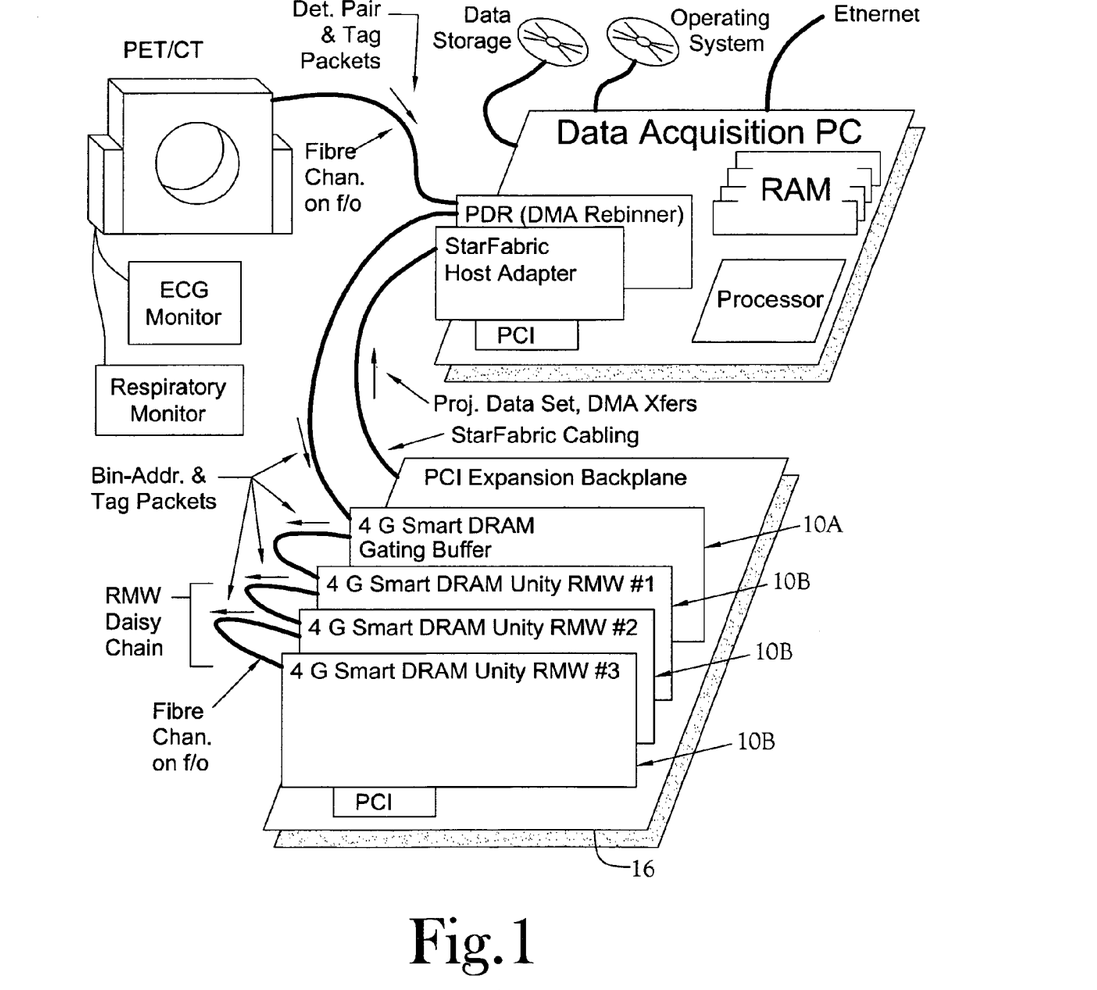
FIG. 1 is a schematic illustration of a PC-based acquisition architecture incorporating four Smart DRAM (SD) peripheral component interconnect (PCI) cards incorporating various features of the present invention, one SD PCI card being shown for on-line gating, i.e., SD Gating Buffer, and three SD PCI cards being shown for on-line unity histogramming, i.e., SD Unity RMW.

FIG. 1 is a schematic illustration of a PC-based acquisition architecture incorporating four Smart DRAM (SD) peripheral component interconnect (PCI) cards of the present invention, illustrated generally at 10. In the illustrated system, the SD PCI card 10 is applied in two ways. One of the four SD PCI cards 10A is used as a Gating Buffer, while the remaining three SD PCI cards 10B are used for unity RMW histogramming. This embodiment principally supports on-line gated PET data acquisition. Histogramming rates in the range from 14 to 19 M events/sec are supported. It will be understood, however, that other rates outside this range may be accomplished using architectures within the scope of the present invention. With an extendible daisy-chain, very large projection data sets are supportable, for example, $10^{12}$ bins.

The Gating Buffer card 10A alternately stores an arriving PET data packet stream into one of two dedicated DRAM 14 banks. (FIG. 2) The two DRAM banks store and retransmit the packet stream in the order of arrival for an entire physiological cycle. This buffering enables on-line rejection of "bad-beat" cycles, e.g., too long or too short in duration, and serves the more complex needs of real-time cardiac/respiratory gating. The Histogramming function provided on the remaining three SD RMW PCI cards 10B of the present invention is such that the heavy on-line RMW burden is eliminated from loading down both the PC-CPU and PC-resident DRAM. A daisy chain of histogramming SD RMW PCI cards 10B is illustrated in FIG. 1 and provides a very high rate of histogramming. For example, histogramming at a rate of 14 to 19 M events/sec is possible. The extendible daisy-chain of SD RMW PCI cards 10B supports large memory banks, limited to $\sim 10^{12}$ bins (1-4 Terabytes) across potentially hundreds of SD RMW PCI cards 10B in the chain, as required. Under a single PC, a multiple PCI Expansion chassis 16 is provided such that a large number of SD RMW PCI cards 10B are supported. The SD RMW PCI design effectively solves the problem of limited address space found in current PC systems. Specifically, a moveable 4 Mbyte PCI DMA window is defined for fast and effective DMA transfers into the PC motherboard of the huge, i.e., not conventionally addressable, sets of projection data. Further, flow control signaling (not fully illustrated) may be sent upstream between the full-duplex FC links 18.

While the architecture in FIG. 1 is significant for on-line gated studies, it is also effective for many other, even more demanding on-line acquisition types. These include, but are not limited to, rapid dynamic, dynamic-gated, continuous bed motion, time-of-flight (TOF), gated-TOF, and correction for patient motion. The present invention further supports both list-mode-only data acquisition as well as for rapid replay in post-acquisition histogramming of previously collected list-mode data.

For effective index/offset control into the potential Terabytes of DRAM space, frame-offset tag packets are used. As a means to direct which frame or phase-segment portion of the bin-space is accessed for RMW activity, these offset-control tag packets are input to the Gating Buffer card 10A under control of PC-OS-based application software. The offset tag packets are intermixed with bin-address event packets. These packets are all output from the Gating Buffer FC port for reception by the down-stream SD RMW PCI cards 10B. The bin-offset values in these tag packets are received and used by the FPGA 12B on each of the down-stream SD RMW PCI cards 10B to instantly direct histogramming into the designated projection frame, i.e., some portion of the memory space across all the histogramming SD RMW PCI cards 10. The use of the Fibre Channel daisy chain to distribute the frame-offset value to all SD RMW PCI cards 10 minimizes the application code interaction with PCI-accessed FPGA-resident control registers, i.e., one frame-offset register access into the SD Gating Buffer card with FC daisy chain distribution of the value avoids the need for multiple and more time-critical PCI registers accessed across multiple SD RMW PCI cards 10. The FPGA 10B on each of SD RMW PCI cards 10B in the chain is directed from the PC operating system via FPGA-resident PCI-loaded registers to respond to only a designated card-size (for example, 4 Gbyte) portion of the available 40-bit projection-data bin space. This bin space is spread across all the SD RMW PCI cards 10B in the chain and is limited to 40-bit indexing. Thus, the offset-control tag-packet mechanism is an effective means to instantly direct bin-address activity into any part of the RMW daisy chain via minimal PCI interaction.

Figure 2:
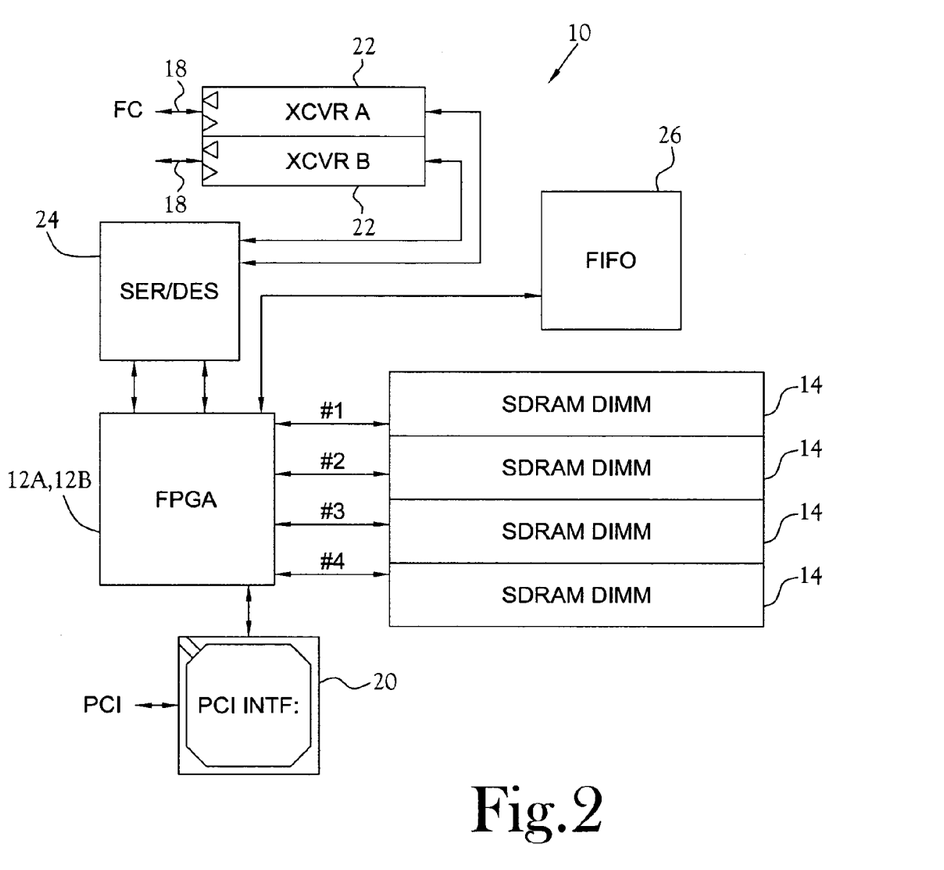
FIG. 2 is a schematic illustration of the component architecture internal to the Smart DRAM PCI card incorporated in the architecture illustrated in FIG. 1.

FIG. 2 is a schematic illustration of the component architecture internal to each SD RMW PCI card 10 of the present invention. Each box in the diagram represents a chip or component on the card 10. A single field programmable gate array (FPGA) 12A, 12B is in communication with the RAM 14 and with the input/output (I/O) flow, including I/O via at least one Fibre Channel (FC) 18 and a PCI interface 20. This architecture achieves maximum flexibility and permits a single board design to service multiple applications. In the illustrated embodiment, four DRAM dual in-line memory modules (DIMMs) 14 are each independently in communication with the FPGA 12A, 12B to permit independent and simultaneous direct memory access (DMA) to each bank, thus optimizing throughput. While DRAM banks 14 are illustrated and described, it will be understood that other RAM configurations may be used within the scope of the present invention. The FPGA 12A, 12B is in communication with each Fibre Channel port 18 via a transceiver 22 and a serializer/deserializer (SERDES) chip 24. Also provided in communication with the FPGA 12A, 12B is a first in, first out (FIFO) memory chip 26.

Figure 3:
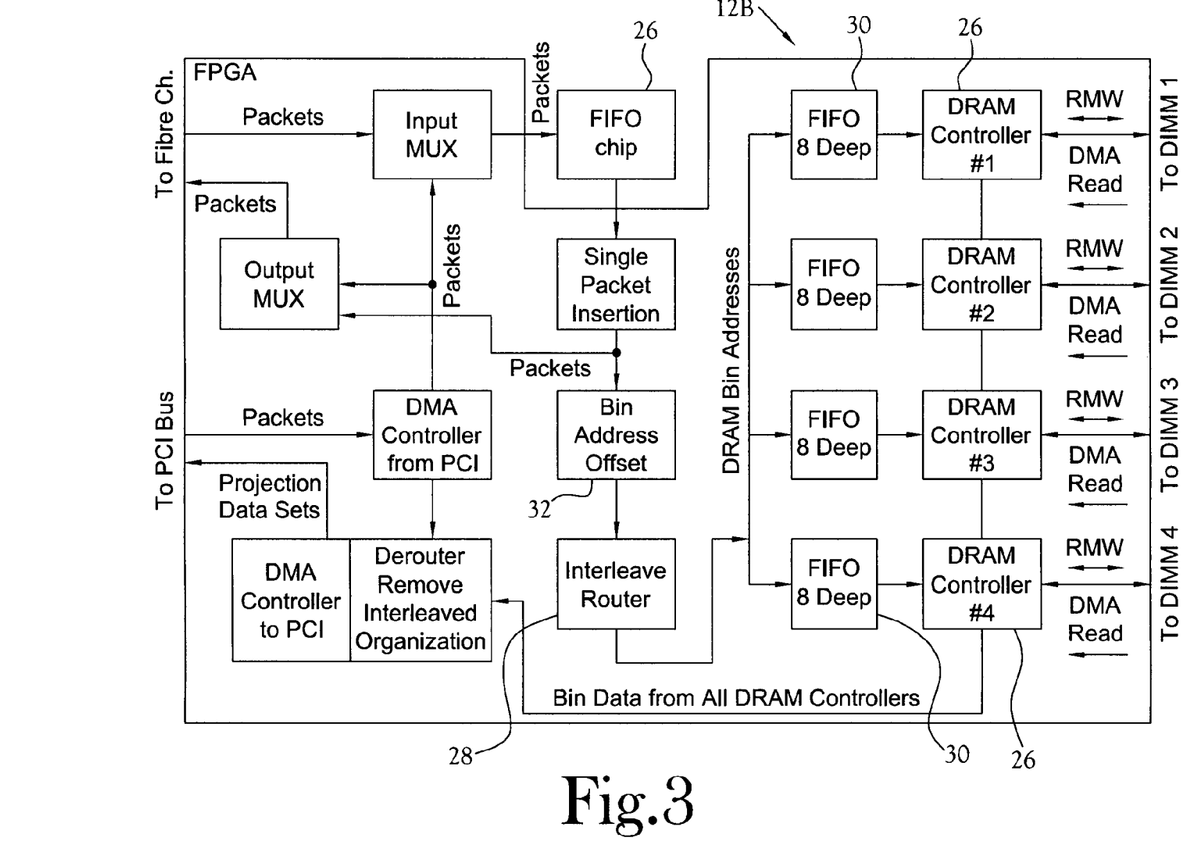
FIG. 3 is a schematic illustration of an FPGA architecture as applied to histogramming.

FIG. 3 is a schematic illustration of the FPGA architecture as applied to histogramming. This embodiment assists in accomplishing a primary method for achieving fast histogramming throughput through the use of quad-interleaving. As shown in FIG. 3, each independent DRAM Controller 26 is actively accessing its own DRAM DIMM 14 for read-modify-write (RMW, +/− Unity and Weighted) transactions into either 8-bit or 16-bit 2's-complement integer bins or 32-bit 2's-complement block-floating bins.

In this configuration, the DRAM address space is "quad-interleaved" with a 4 M byte "granularity." This means that normal memory space content ordering of "ABCDEFGH . . . " where each letter represents 4 M bytes of the projection data space is here intentionally reordered to be "AE . . . " for DIMM1, "BF . . . " for DIMM2, "CG . . . " for DIMM3 and "DH . . . " for DIMM4. An Interleave Router 28 distributes the first four data packets A-B-C-D in order between DIMM1, DIMM2, DIMM3 and DIMM4. This interleaving helps ensure that the normal distribution of LOR-to-bin mapping across the projection data space will load all four DRAM controllers 26 with nearly equal RMW rates, largely independent of the distribution of activity in the PET FOV. Typical whole-body PET projection data spaces are much larger than 4 M bytes. The FPGA 12B automatically "re-orders" the internal quad-interleaved 4 M byte organization upon DMA transfer of projection data out onto the PCI bus, thereby eliminating any user re-assembly burden. In addition, the set-of-4 "FIFO 8 Deep" blocks 30 in FIG. 3 serve to greatly reduce the chance of packet pile-up and loss. As mentioned, the SD RMW card 10B design also supports control methods, i.e., frame-offset tag packet, to quickly offset the arriving bin-address into most any arbitrary portion of the local DRAM space and even across multiple cards in the daisy chain. This bin-address offset control is applied in the "Bin Address Offset" block 32 of FIG. 3 and is critically important for real-time control of multiple-frame dynamic or multiple-phase-segment gated studies.

In testing, the SD RMW PCI card 10B of the present invention has demonstrated RMW (+/− unity) histogramming of real PET data at sustained rates in excess of 14 M events/sec. For one of these tests, over 14 billion ($10^9$) PET 32-bit bin-address list-mode packets were successfully replayed for histogramming in 17 minutes. In this case histogramming speed was primarily limited by the PC disk system. From the resulting 640 M byte projection data set generated by the SD RMW PCI card 10B, a viable 3-D PET image was produced off-card using conventional image reconstruction. Early observations show that data transfers of DRAM contents from the SD RMW PCI card via PCI bus to PC-motherboard DRAM are roughly 117 M bytes/sec for 32/33 PCI slot installations and 146 M bytes/sec for 64/66 PCI slot installation.

Figure 4:
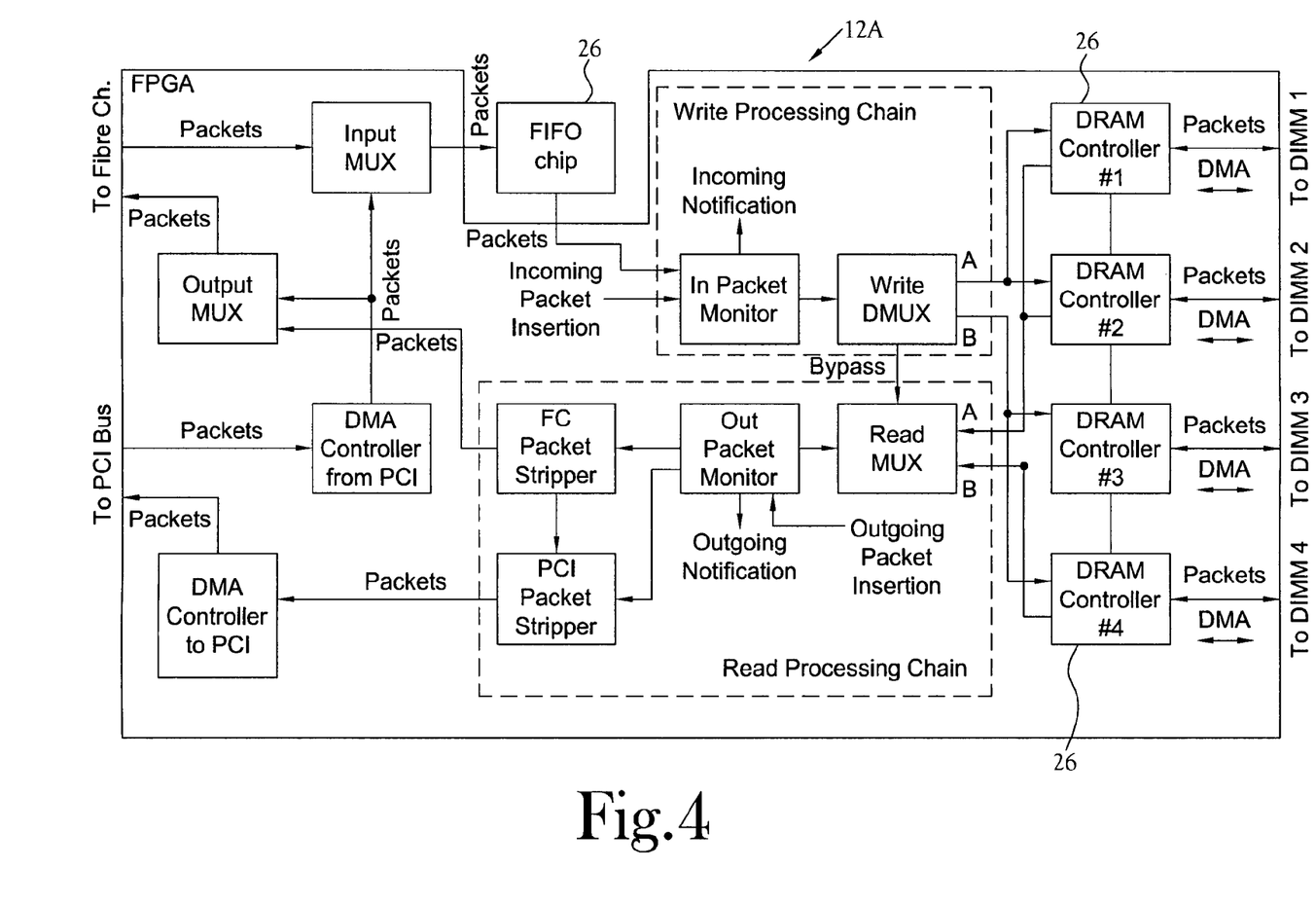
FIG. 4 is a schematic illustration of the FPGA architecture as applied to the Gating Buffer function.

FIG. 4 is a schematic illustration of the FPGA 12A architecture as applied to the Gating Buffer function. In this embodiment, the FPGA 12A and DIMMs 14 are applied without interleaving or histogramming. The Gating SD RMW PCI card 10A is provided primarily to store, or buffer, packets in the order of arrival into one of two DRAM 14 banks. While one bank is loading with data packets arriving in real time via FC input port 18, the other bank is typically unloading via FC output port. Data packet output is controlled by operating system-resident application code which drives autonomous FPGA-resident DMA controllers. The PET packet stream arriving at the Gating Buffer is interspersed with both LOR (event) packets and other non-event (tag) packets. Tag packet content includes elapsed milliseconds, cardiac R-wave, and respiratory phase data. Because the buffered event-and-tag-packet data stream is temporarily stored in local DRAM, more time is available for operating system control of how this data is handled. For example, packets may be directed for down-stream histogramming into specific frames. In one embodiment, the LOR bin-address packet data is histogrammed into different projection-data frames depending on the cardiac phase. This phase may be determined by the elapsed-time tag packet content found in the Gating Buffer relative to any cardiac R-wave tag packets present. The control of which phase-segment frame is targeted for each designated section of the event stream is provided by the afore-mentioned bin-address offset tag control.

Figure 5:
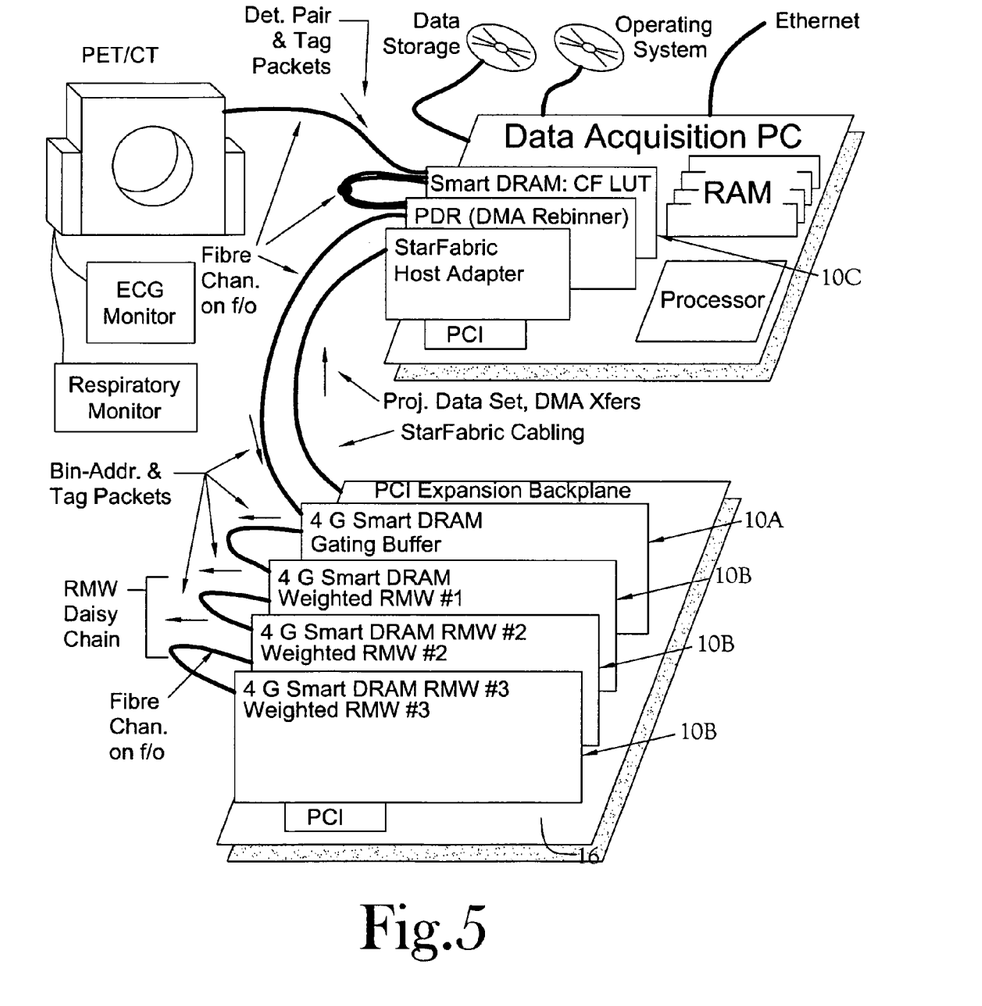
FIG. 5 is a schematic illustration of a PC-based acquisition architecture incorporating five Smart DRAM (SD) peripheral component interconnect (PCI) cards incorporating various features of the present invention, one SD PCI card being shown for on-line normalization, i.e., SD CF LUT, one SD card being shown for on-line gating, i.e., SD Gating Buffer, and three SD PCI cards shown for on-line weighted histogramming, i.e., SD Weighted RMW.

FIG. 5. is a schematic illustration of a second PC-based acquisition architecture incorporating five SD PCI cards 10 of the present invention. In the illustrated system, the SD PCI card 10 is applied in three ways. One of the five SD PCI cards 10 is used as a normalization (correction factor, CF) look-up table (LUT). Another SD PCI card, i.e., SD Gating Buffer, is used in a manner similar to that in FIG. 1., with the exception that the event packets received via the Fibre Channel, processed, and then retransmitted via the Fibre Channel, are each 64-bit weighted bin-address packets. Specifically, each event packet contains an extra field, the 16-bit CF value as added by the SD CF LUT PCI card. The remaining 3 SD PCI cards are all configured to support weighted histogramming, namely, SD Weighted RMW, with each event packet transmitted down the Fibre Channel daisy chain being of the type, 64-bit weighted bin-address.

As shown in FIG. 5, the SD CF LUT PCI card 10 of the present invention is useful for on-line event-by-event normalization. On-line normalization processing is useful in supporting, for example, continuous bed motion and correction of inadvertent patient motion. Event-by-event normalization includes at least the steps of correction value look-up in look up tables (LUTs) resident in memory and weighted histogramming.

For the correction value look-up function, the local DRAM is loaded prior to the start of the acquisition with a PET normalization correction matrix, which is an array of scalar values which reflect the reciprocal of the varied gamma detection efficiencies as pre-determined for each detector pair. As each detector-pair packet arrives via an FC port from the PET Gantry, each respective 16-bit scalar correction value, in block-floating format, is extracted from the local DRAM content. The index into the local DRAM is formed by the FPGA from the detector-pair packet content, namely, the crystal-pair indexes. Each extracted value is loaded into a designated field within each detector-pair packet. This modified packet with correction value, which is potentially larger than its original size, is then transmitted for further processing via the out-going FC port. The FC output is, in one embodiment, connected to a custom PCI card for next-stage on-line processing such as nearest-neighbor rebinning such as in the PETLINK™ DMA Rebinner (PDR) card illustrated in both FIGS. 1 and 5.

For the weighted histogramming function, the SD RMW PCI card 10 performs histogramming in much the same manner as previously described. However, for on-line normalization, the daisy-chain of SD RMW PCI cards are FPGA-configured for weighted histogramming. For this case, each DRAM-resident RMW bin is a 32-bit 2's block-floating complement value. The event packets input via the FC port are intermixed with conventional tag packets. These event packets are called 64-bit weighted bin-address event packets. The new packets contain not only the traditional Prompt/Delayed (P/D) bit but also a bin-address field and the correction-value field. The more traditional PET histogramming, without the complexity of weighted histogramming, merely employs +/- unity RMW cycles into 8-bit or 16-bit bins in memory. By contrast, for weighted histogramming, the correction value is added/subtracted to/from the respective bin in DRAM memory, depending on the P/D bit. In this mode of operation, the bin-address value is applied as a quad-byte index into local DRAM. Because both the correction value and the bin content are treated as block floating, the FPGA performs only signed-integer arithmetic for the RMW memory cycles. The result of on-line weighted histogramming is that all projection-data sets resident in local DRAM are inherently corrected for pre-normalized detector efficiency variations during the entirety of the acquisition.

Typically, the block-floating format has an implied decimal point between bits 10 & 11. This implied decimal location applies uniformly to both a 16-bit correction value and a 32-bit bin value. This assumption provides for normalization values—for example, an unsigned block-floating 16-bit correction value—to range from zero to values as high as 31.00 (5 bits to left of decimal) with a precision limit of +/-0.00024 (11 bits to right of decimal). A zero correction value may be used to effectively force a bad LOR to be ignored, i.e., a case where a pre-measured correction value is judged too extreme to be desirable. Similarly, the signed block-floating 32-bit bin values range as +/-1048575 (20-bits plus sign bit to left of decimal). The 32-bit bin precision limit is the same (+/-0.00024) as the prior example. Other correction factors supported by this specific choice for the location of the implied decimal include: zero, 0.04883, 0.04916, 1.0, 1.0005, 30.0, 30.0005, etc. Other trade-offs between range and precision, i.e., by selecting an alternate location for the implied decimal point are within the scope of the present invention and may also find application. In this context, the chosen location for the implied decimal point is not determined or limited by the FPGA configuration.

There is a small accumulation of error in on-line normalization that occurs with this limited-precision block-floating approach. Consider a specific 32-bit bin in the projection space that has been indexed by, for example, 100 LOR, i.e., this bin has seen 100 weighted-RMW cycles. If the 100 RMW cycles involve correction factors that are all near unity, ranging from 0.845 to 1.155, for example, there is an accumulating error on the final 32-bit bin value that might in a rare case approach 100*0.00024=0.024. This error is roughly 0.024% of the final bin value of approximately 100. Compared to the percent standard deviation for a statistical count of 100, i.e., 10%, this example for a rather extreme case with this very small magnitude of error (0.024%) validates the use of the SD Weighted RMW PCI card for limited-precision on-line normalization method.

From the foregoing description, it will be recognized by those skilled in the art that a device for improved on-line histogramming of data acquired in a Positron Emission Tomography (PET) scan has been provided. The device includes a plurality of Smart DRAM peripheral component interconnect (SD RMW PCI) cards adapted to permit very fast read-modify-write (RMW, +/- Unity and Weighted) histogramming memory cycles, and to permit large amounts of RMW memory to be effectively controlled from a single PC motherboard running a single operating system (OS). The SD RMW PCI cards are individually adapted to be used either as a Gating Buffer, for normalization look up, or for histogramming. The present invention supports on-line gated PET data acquisition.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, we claim:

1. A device for on-line histogramming of data acquired in a Positron Emission Tomography (PET) scan, said device comprising:
    at least one peripheral component interconnect (PCI) card configured to function as one of a gating buffer, a histogramming device, and a normalization buffer,
        said at least one PCI card including:
            a field programmable gate array (FPGA);
            at least one memory device in communication with said FPGA;
                wherein said memory device included a plurality of DRAM devices,
                    wherein each DRAM device is independently in communication with said FPGA, whereby independent and simultaneous direct memory access (DMA) to each of said plurality of DRAM devices is permitted;
            at least one input/output (I/O) device in communication with said FPGA; and
            a first in first out (FIFO) memory chip in communication with the FPGA;
        wherein at least one said PCI card us configured to function as a gating buffer in which:
            said DRAM devices defines a first dedicated DRAM bank and a second dedicated DRAM bank, and
            an arriving PET data packet stream is alternately written into said first dedicated DRAM bank and said second dedicated DRAM bank, while data previously written into the other of said first dedicated DRAM bank and said second dedicated DRAM bank is being read.

2. The device of claim 1 wherein said at least one I/O device includes:
    at least one Fibre Channel (FC), said device further comprising at least one transceiver and a data serializer/deserializer (SERDES) device in communication between said FPGA and said at least one FC; and
    a PCI interface.

3. The device of claim 1 wherein frame offset-control tag packets are input to said PCI card to identify a portion of bin-space to be accessed for read-modify-write (RMW) activity, said frame offset-control tag packets being intermixed with bin-address event packets within said PCI card and output from said PCI card to instantly direct histogramming performed downstream of said PCI card.

4. The device of claim 1 wherein correction factors are inserted into bin-address event packets within said PCI card.

5. The device of claim 4 wherein said correction factors are utilized during on-line PET data acquisition in block-floating format.

6. The device of claim 5 wherein said PCI card is configured to function as a normalization buffer for on-line event-by-event normalization including at least the steps of looking up correction values in look up tables (LUTs) and weighted histogramming.

7. A device for on-line histogramming of data acquired in a Position Emmission Tomography (PET) scan, said device comprising:
   a plurality of peripheral component interconnect (PCI) card configured to function as histogramming device, said at least PCI card including:
      a field programmable gate array (FPGA);
      at least one memory device in communication with said FPGA;
         wherein said memory device includes a plurality of DRAM devices,
            wherein each DRAM device is independently in communication with said FPGA, whereby independent and simultaneous direct memory access (DMA) to each of said plurality of DRAM devices is permitted;
      at least one input/output (I/O) device in communication with said FPGA; and
      a first in, first out (FIFO) memory chip in communication with the FPGA; and
   a PCI expansion chassis for interfacing each of said plurality of PCI cards, each of said plurality of PCI cards being in serial communication in a daisy chain method;
   said FPGA including:
      a plurality of DRAM controllers, one each of said plurality of DRAM controllers being provided for individually controlling one of said plurality of DRAM devices; and
      an interleave router for distributing RMW activity by means of either of dual and quad interleaving between said plurality of DRAM devices via said respective plurality of DRAM controllers, said FPGA reordering said data packets upon DMA transfer of projection data.

8. The device of claim 7 wherein said PCI card is configured to function as a normalization buffer for on-line event-by-event normalization including at least the steps of looking up correction values in look up tables (LUTs) and weighted histogramming.

9. The device of claim 7 wherein said PCI card is adapted to perform at least one function selected from at least rapid dynamic, dynamic-gated, continuous bed motion correction, time-of-flight (TOF), gated-TOF, and correction of patient motion.

10. The device of claim 7 wherein said PCI card is adapted for list-mode-only data acquisition as well as for rapid replay in post-acquisition histogramming of previously collected list-mode data.

11. A device for on-line histogramming of data acquired in a Positron Emission Tomography (PET) scan, said device comprising:
   a first peripheral component interconnect (PCI) card configured to function as a gating buffer;
   a plurality of second PCI cards configured to perform a histogramming function, each of said plurality of second PCI cards being in serial communication in a daisy chain method;
   each of said first PCI card and said plurality of second PCI cards including:
      a field programmable gate array (FPGA);
      at least one memory device in communication with said FPGA;
         each said memory device including a plurality of DRAM devices, wherein each of said plurality of DRAM devices is independently in communication with said FPGA, whereby independent and simultaneous direct memory access (DMA) to each of said plurality of DRAM devices is permitted; and
         wherein said plurality of DRAM devices defines a first dedicated DRAM bank and a second dedicated DRAM bank, wherein an arriving PET data packet stream is alternately written into one said first dedicated DRAM bank and said second dedicated DRAM bank, while data previously written into the other of said first dedicated DRAM bank and said second dedicated DRAM bank is being read;
      at least one input/output (I/O) device in communication with said FPGA; and
      a first in, first out (FIFO) memory chip in communication with the FPGA.

12. The device of claim 11 wherein said at least one I/O device includes:
   at least one Fibre Channel (FC), said device further comprising at least one transceiver and a data serializer/deserializer (SERDES) device in communication between said FPGA and said at least one FC; and
   a PCI interface.

13. The device of claim 11 wherein frame offset-control tag packets are input to said PCI card to identify a portion of bin-space to be accessed for read-modify-write (RMW) activity, said frame offset-control tag packets being intermixed with bin-address event packets within said PCI card and output from said PCI card to instantly direct histogramming performed downstream of said PCI card.

14. The device of claim 11 wherein said FPGA includes:
   a plurality of DRAM controllers, one each of said plurality of DRAM controllers being provided for individually controlling one of said plurality of DRAM devices; and
   an interleave router for distributing RMW activity by means of either of dual and quad interleaving between said plurality of DRAM devices via said respective plurality of DRAM controllers, said FPGA reordering said data packets upon DMA transfer of projection data.

15. A device for on-line histogramming of data acquired in a Positron Emission Tomography (PET) scan, said device comprising:
   a first peripheral component interconnect (PCI) card configured to function as a gating buffer;
   a plurality of second PCI cards configured to perform a histogramming function, each of said plurality of second PCI cards being in serial communication in a daisy chain method;
      each of said first PCI card and said plurality of second PCI cards including:

a field programmable gate array (FPGA);
a plurality of DRAM devices, wherein each of said plurality of DRAM devices is independently in communication with said FPGA, whereby independent and simultaneous direct memory access (DMA) to each of said plurality of DRAM devices is permitted and throughput is optimized;
at least one input/output (I/O) device in communication with said FPGA, said at least on I/O device includes:
at least one Fibre Channel (FC), said device further comprising at least one transceiver and a data serializer/deserializer (SERDES) device in communication between said FPGA and said at least one FC; and
a PCI interface; and
a first in, first out (FIFO) memory chip in communication with the FPGA;
wherein said plurality of DRAM devices associated with said first PCI card defines a first dedicated DRAM bank and a second dedicated DRAM bank, wherein an arriving PET data packet stream is alternately written into one said first dedicated DRAM bank and said second dedicated DRAM bank, while data previously written into the other of said first dedicated DRAM bank and said second dedicated DRAM bank is being read, and wherein frame offset-control tag packets are input to said first PCI card to identify a portion of bin-space to be accessed for read-modify-write (RMW) activity, said frame offset-control tag packets being intermixed with bin-address event packets within said first PCI card and output from said first PCI card to instantly direct histogramming performed by said plurality of said second PCI cards; and
wherein said FPGA associated with each of said plurality of second PCI cards includes:
a plurality of DRAM controllers, one each of said plurality of DRAM controllers being provided for individually controlling one of said plurality of DRAM devices; and
an interleave router for distributing RMW activity by means of either of dual and quad interleaving between said plurality of DRAM devices via said respective plurality of DRAM controllers, said FPGA reordering said data packets upon DMA transfer of projection data.

* * * * *